United States Patent
Arumi et al.

(10) Patent No.: US 6,945,984 B2
(45) Date of Patent: Sep. 20, 2005

(54) MICRO SURGICAL INSTRUMENT

(75) Inventors: Jose Garcia Arumi, Barcelona (ES); Werner Maag, Glarus (CH); Oliver Jud, Löhningen (CH)

(73) Assignee: Alcon Grieshaber AG, Schaffhausen (CH)

( * ) Notice: Subject to any disclaimer, the term of this patent is extended or adjusted under 35 U.S.C. 154(b) by 0 days.

(21) Appl. No.: 09/935,869

(22) Filed: Aug. 23, 2001

(65) Prior Publication Data
US 2003/0040773 A1 Feb. 27, 2003

(51) Int. Cl.$^7$ .............................................. A61B 17/12
(52) U.S. Cl. ...................................... 606/205; 606/207
(58) Field of Search ..................... 606/205–211, 151, 606/107

(56) References Cited

U.S. PATENT DOCUMENTS

| | | | | |
|---|---|---|---|---|
| 2,549,731 A | * | 4/1951 | Wattley | 606/206 |
| 4,427,014 A | * | 1/1984 | Bel et al. | 606/206 |
| 4,467,802 A | * | 8/1984 | Maslanka | 606/206 |
| 4,655,219 A | * | 4/1987 | Petruzzi | 606/206 |
| 5,222,973 A | * | 6/1993 | Sharpe et al. | 606/206 |
| 5,486,185 A | * | 1/1996 | Freitas et al. | 606/206 |
| 5,514,148 A | * | 5/1996 | Smith, III | 606/151 |
| 5,735,849 A | * | 4/1998 | Baden et al. | 606/205 |
| 5,746,770 A | * | 5/1998 | Zeitels et al. | 606/207 |
| 5,797,958 A | * | 8/1998 | Yoon | 606/207 |
| 5,893,873 A | | 4/1999 | Rader et al. | |
| 6,254,530 B1 | | 7/2001 | Ryan, Jr. | |

FOREIGN PATENT DOCUMENTS

WO    WO 01/37767 A1    5/2001

* cited by examiner

*Primary Examiner*—Anhtuan T. Nguyen
*Assistant Examiner*—Jessica R. Baxter
(74) *Attorney, Agent, or Firm*—Henry M. Feiereisen; Ursula B. Day

(57) ABSTRACT

A microsurgical instrument is described for ophthalmologic microsurgery in the eye which comprises a housing configured as a handle with a functional unit supporting a probe and a rod co-axially supported in the probe having a head piece configured as a grasping element with two arms that can be brought into a spread apart first position and a second closed position, wherein each arm has a recess which upon closing are flush pressed together thereby forming a larger recess for unobstructed grasping, retaining and holding microstructures such as blood vessels without squeezing or pinching the microstructures.

19 Claims, 6 Drawing Sheets

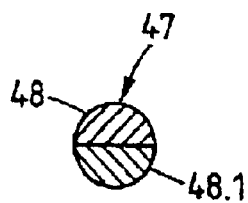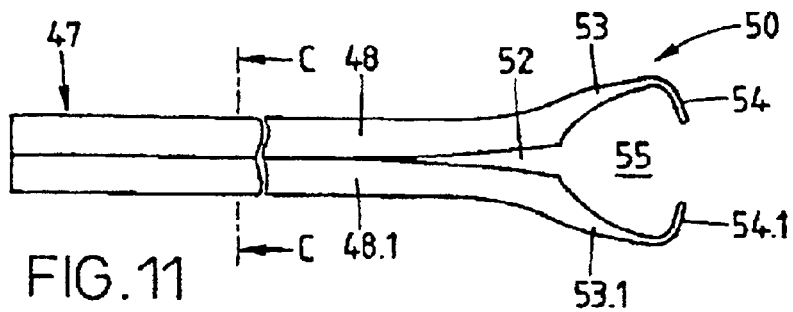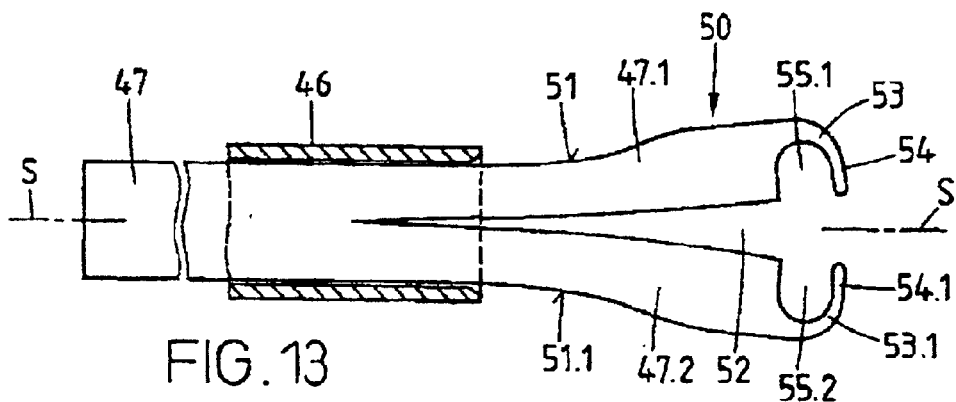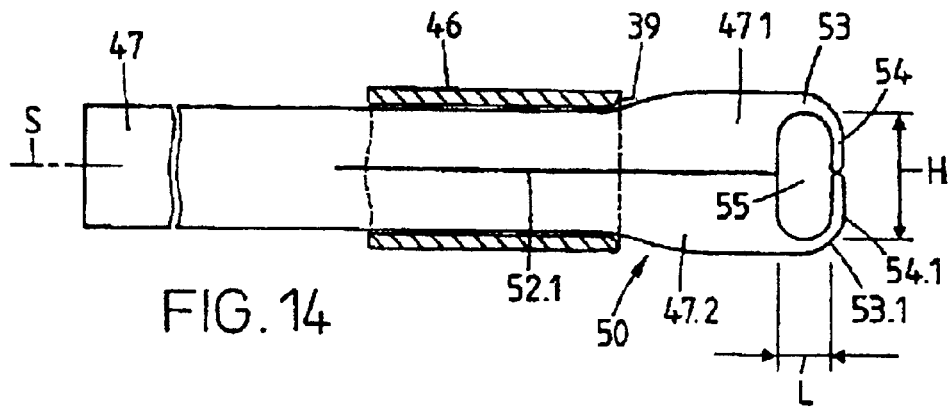

MICRO SURGICAL INSTRUMENT

BACKGROUND OF THE INVENTION

The present invention relates to a microsurgical instrument, in particular to a ophthalmologic instrument for use especially but not exclusively in surgery of the retina of an eye of the type having a housing configured as a handle and an axial probe operatively connected to the housing, wherein the probe is configured for receiving an axially extended rod with a head piece configured for microsurgical procedures.

The present invention concerns problems that arise in surgical treatment of retinal diseases, as for example resulting from hypertonia, or other vascular changes. In a typical disease where vascular changes are the origin, a venous branch occlusion (phlebemphraxis) can occur at the crossing point of an artery and a vein. In the area of the crossing the artery and the vein are surrounded by a substantially transparent skin sheath or membrane and the artery which overlays the vein can press on the vein such that the vein may be squeezed off in such a manner that an occlusion occurs resulting in an obstruction of the blood flow.

Experiments have shown that by surgically cutting or removing this skin membrane by means of an ophthalmologic instrument, venous branch occlusions can be substantially eliminated or prevented. During microsurgery the transparent skin membrane is removed and the artery separated from the vein for blood flow to resume in this area. When using the conventional microsurgical instruments separation of the artery from the vein may result in the injury to the artery or injury to the underlying vein. Furthermore, the artery may be "pinched" by the microsurgical instrument during separation leading to trauma or injury of these delicate blood vessels.

It would thus be desirable and advantageous to provide an improved surgical instrument with which these shortcomings can be overcome.

When carrying out this micro surgery it is important that the artery is being moved away from the vein by a small pull motion in such a manner that the vein is being laid free but that the pull motion on the artery is carried out without the artery being squeezed off, pinched or constricted in any way.

SUMMARY OF THE INVENTION

According to one aspect of the present invention an improved ophthalmologic instrument is provided which is designed to obviate the afore-stated shortcomings and which is configured for retaining these delicate blood vessels by providing an instrument for easy retention and grasping of the microstructures.

In another aspect, the present invention provides an improved ophthalmologic instrument with two grasping arms that permit freely holding delicate micro structures such as blood vessels or similar.

These aspects, and others which will become apparent hereinafter, are attained in accordance with the present invention, wherein the microsurgical instrument has a probe attached with a rod axially disposed therein, the rod has a head piece from which two arms extend in axial direction which are separated by a slot and which can be spread apart relative to each other for a spring elastic pretensioning. At their respective front ends, the arms are so configured that when moving the arms toward each other in a closing motion, a recess is formed which is dimensioned perpendicular relative to the rod axis in which recess a microstructure such as a blood vessel can be easily and freely retained and held.

BRIEF DESCRIPTION OF THE DRAWING

The above and other aspects, features and advantages of the present invention will now be described in more detail with reference to the accompanying drawing in which:

FIG. 11 is another variation of the rod with the integrally formed grasping element of FIG. 6 in an open position;

FIG. 12 is a section of the rod along line C—C in FIG. 11;

FIG. 13 is a section of the probe of FIG. 6 showing a second variation of the grasping element integrally formed at the rod in an open position;

FIG. 14 is a view of the probe of FIG. 13 with the grasping element in a closed position;

DETAILED DESCRIPTION OF PREFERRED EMBODIMENTS

Figure 1:
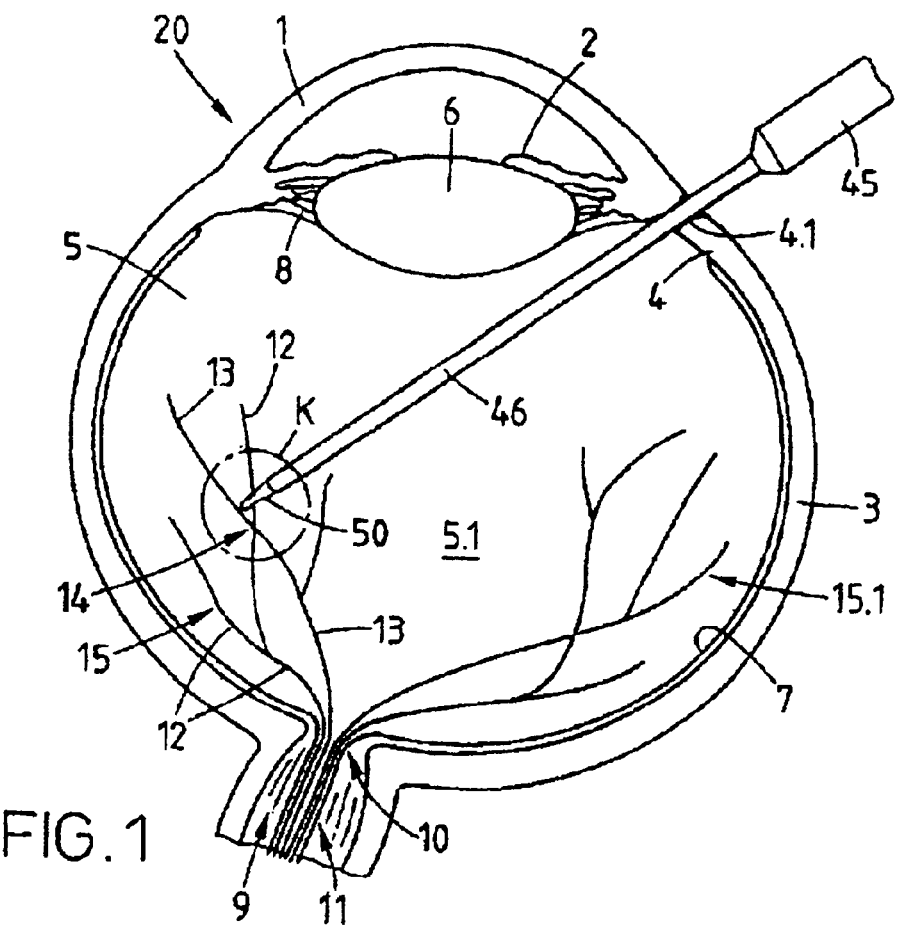
FIG. 1 is a horizontal section on an enlarged scale of an eye during intra-ocular surgery with a surgical instrument according to the invention inserted into the vitreous humor in the vicinity of crossed blood vessels which is indicated by a circle K.

Throughout all the Figures, same or corresponding elements are generally indicated by same reference numerals.

Turning now to the drawing, and in particular to FIG. 1, there is shown in a schematic horizontal section on an enlarged scale a human eye, generally designated by reference numeral 20 and including the cornea 1, the iris 2, the sclera 3, the pars plana 4, the vitreous humor 5 with its vitreous chamber 5.1, the lens 6, the retina 7, the ciliary processes 8, (zonule fibers). In the eye background the disc shaped optic disk 10 is shown where the nerve fibers of the retina are gathered into the optic nerve bundle 9 from where they leave the eye.

Figure 2:
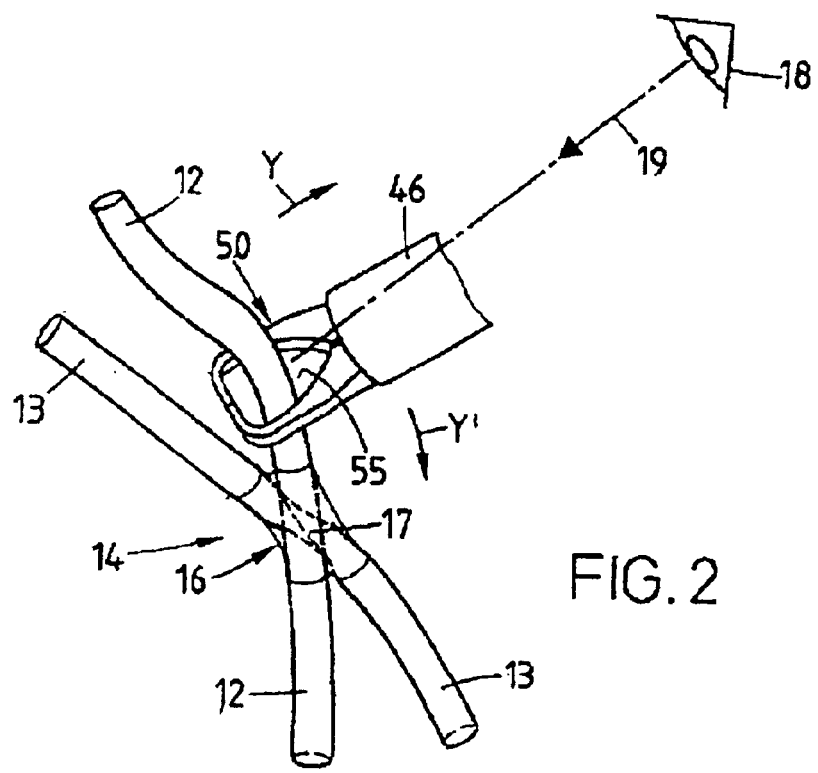
FIG. 2 is a partial view of the section in the eye circled as K in FIG. 1, with the blood vessel system seen is in a 3-dimensional view with a blood vessel being held by the grasping element of the microsurgical instrument as during micro surgery.

The central artery and venous system generally designated with 11 which is surrounded by the optic nerve bundle 9 branches into several branches in the optical disc 10 jointly forming the two blood vessel systems 15 and 15.1. The blood vessel system 15 which is schematically depicted in FIG. 1 comprises the arteries 12 and veins 13 which for example are shown in crossed-over position in the area designated as 14 and are joined together by a relatively thin, transparent sheath or membrane of skin (FIG. 2). Arteries 12 and veins 13 of each of the blood vessel systems 15, respectively 15.1 each have an outer diameter of about 0.1 mm to 0.15 mm.

There is further shown in FIG. 1 a probe 46, which is configured as an elongated needle for insertion through a surgical incision 4.1 at the area of the pars plana 4 into the vitreous humor 5.1. The probe 46 has a diameter of about 1 mm and has an inner diameter of about 0.8 mm. Axially disposed within the probe 46 is a rod with a front end projecting from the probe 46; a head piece 50 is disposed at the front end of the rod which is configured for the grasping, retaining and holding of micro structures. Preferred embodiments and variations of the headpiece 50, which is configured as a grasping element, are described in the following paragraphs.

In FIG. 2 the area 14 of the blood vessel system 15 which has been designated with a circle K in FIG. 1 is depicted in a 3-dimensional and enlarged view, where a portion of the artery 12 which is overlying the vein 13 seen as lying underneath the artery 12 is retained by the grasping element of the head piece 50 projecting from the probe 46. As schematically shown in FIG. 2, the artery 12 and vein 13 situated in area 14 are surrounded by a substantially transparent sheath or membrane of skin 16 and joined together thereby. In the area where the artery 12 overlays the vein 13, venous branch occlusion can occur, a condition wherein the vein 13 is being pressed together by the artery 12 which can result in the vein being squeezed or pinched which can lead to partial or complete occlusion. By cutting open the skin sheath 16, as for example seen in FIG. 2 by the schematically represented line 17, or by removing the skin sheath 16 altogether, such venous branch occlusions can be substantially prevented or eliminated when the artery is moved such that the vein is no longer squeezed or pinched. Such a microsurgical procedure requires that while the step of cutting or removing the skin sheath is carried out, the artery 12 is simultaneously removed by a pull motion oriented in the direction of arrow Y and Y' as indicated in FIG. 2 by means of the head piece 50 of the instrument but without the slightest pinching or squeezing effect on the vein 13.

The headpiece 50 with the effective recess 55 is preferably configured in such a manner that the artery 12 of the eye 18 can be viewed by the surgeon during the microsurgical procedure along an axis 19 as schematically depicted in FIG. 2.

Figure 3:
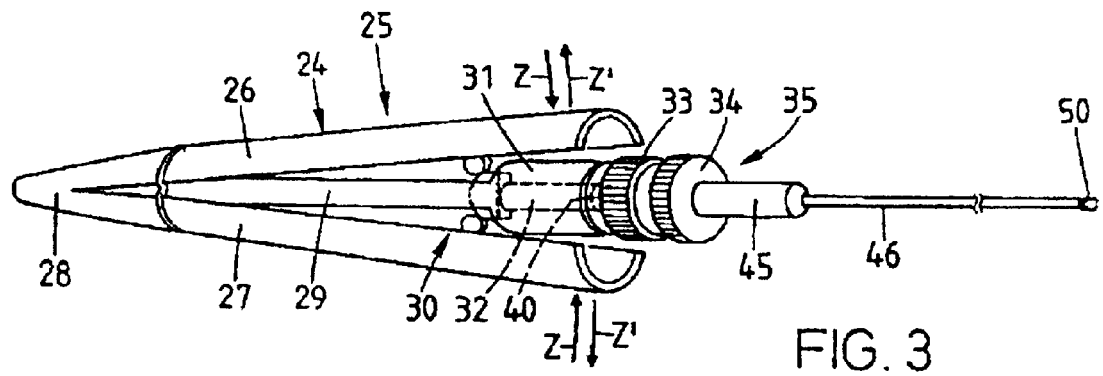
FIG. 3 is a perspective view of the surgical instrument with the probe and the grasping element disposed therein.

In FIG. 3 another embodiment of an ophthalmologic instrument 25 is shown, which is provided with a headpiece 50 configured as a grasping element especially designed for grasping, retaining and holding microstructures. Instrument 25 comprises essentially a housing 24 that is configured as a handle with the housing formed from two semicircular housing parts 26 and 27 that are tightly held together at their distal end with closure cap 28. Disposed between the two housing parts 26 and 27 is a carrying arm 29 operatively connected to a spreader mechanism 30 and a guide piece 31. The carrying arm 29 is configured for threadable engagement to a functional unit 35, which unit is provided with an actuator 40 and a probe 46 (FIGS. 4, 5), wherein the actuator 40 is operatively connected to a sliding pin 32 supported in the guide piece 31 and the spreader mechanism 30.

In the embodiment of the instrument 25 as shown in FIG. 3, when the two housing parts 26, 27 are moved in the direction of arrow Z, then the sliding pin 32 which is disposed within the guide piece 31 is slidably movable by means of the spreader mechanism in axial direction. When the two housing parts 26, 27 are moved in direction of arrow Z' the sliding pin 32 is axially slidably moved in opposite direction by means of the restoring force of pressure spring 44 which is disposed in the functional unit 35 (FIGS. 4, 5).

Figure 4:
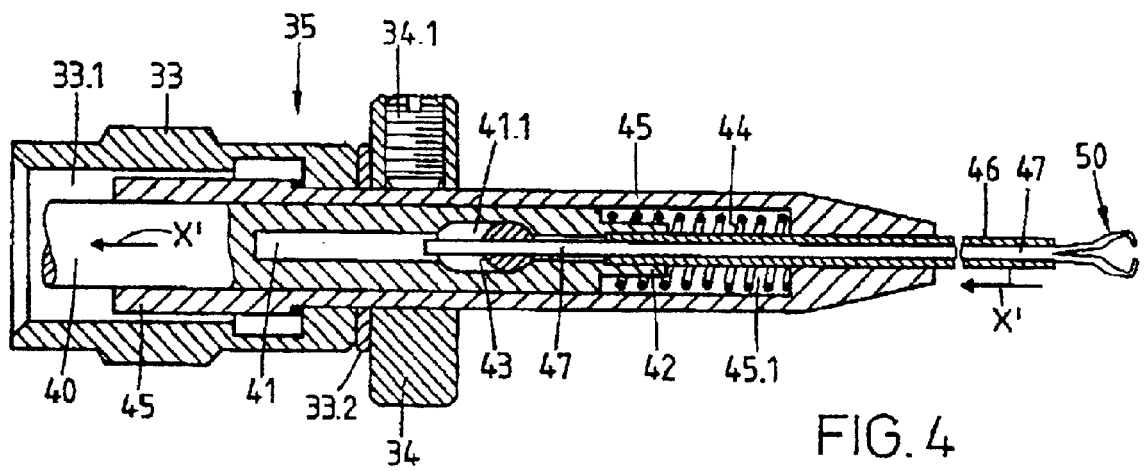
FIG. 4 is a section view of the functional unit on an enlarged scale with the probe and a rod disposed therein with the schematically depicted grasping element.

FIG. 4 shows a section of the functional unit 35 on an enlarged scale wherein a swivel nut 33 has a recess 33.1 with a guide sleeve 45 supported therein, the guide sleeve 45 has an intermediary ring 33.2 and a set collar 34 disposed on its outer diameter. Set collar 34 is held at the guide sleeve 45 with a screwed in setscrew 34.1, combining all parts into a constructional unit. The actuator 40, which has at one end a cylindrical part 42 set off from the actuator 40 and which cooperates with the sliding pin 32 in a manner not shown in detail here is disposed in a recess 45.1 in guide sleeve 45. Pressure spring 44 is supported and biassed in the recess 45.1 of the guide sleeve 45 of the cylindrical part 42.

Actuator 40 has a blind bore 41 and a corresponding recess 41.1. which radially penetrates the actuator 40. The blind bore 41 is configured for receiving and supporting the probe 46 which is configured as a hollow needle with an elongated rod 47 supported in the tube shaped probe 46. The rod 47 is disposed at the proximate free end of the headpiece 50, preferably the headpiece 50 is integral with the end of rod 47. The tube-shaped probe 46 is operatively connected with the actuator in a manner not shown here in detail, for example by a glue-, solder- or weld connection. The end of the rod 47 which is supported in the probe 46 is secured against axial displacement by means of at least one set screw 43 which is radially screwed into guide sleeve 45. Head piece 50 which configured for grasping, retaining and holding micro structures is mounted at the other end of the rod 47 which projects from the tube shaped probe. In FIG. 4, head piece 50 is shown in substantially open position due to the probe 46 being retracted in the direction of arrow X'.

Figure 5:
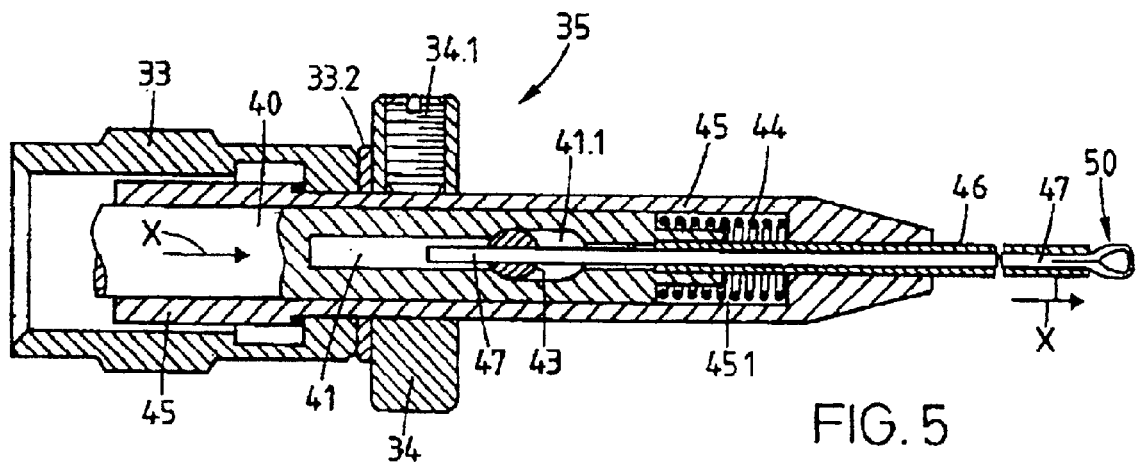
FIG. 5 shows the functional unit according to FIG. 4 with the grasping element in a closed position.

FIG. 5 shows the afore-described functional unit 35 with each of its elements. In a variation of the unit as shown in FIG. 4, the actuator 40 is off-set in axial direction according to arrow X against the restoring force of the pressure spring 44 and relative to the rod 47 which is secured with the guide sleeve 45 by means of the set screw 34.1. The movement of the tube shaped probe 46 in axial direction relative to the head piece disposed at the rod 47 is realized by an ophthalmologist's use of the embodiment of instrument 25 in as seen in FIG. 3.

In the following paragraphs, the various embodiments of the rod 47 disposed in the tube shaped probe 46 are described in conjunction with the head piece which may be for example integrally formed with the rod and which is configured as a grasping element, wherein the rod is generally designated with 47 and the head piece generally designated with 50.

Figure 6:
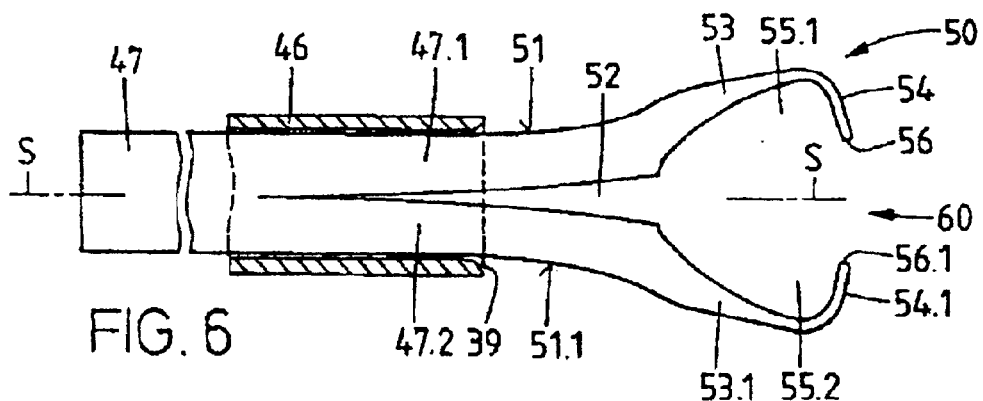
FIG. 6 is a partial section on an enlarged scale of the tube shaped probe with a first variation of the grasping element integrally formed at the rod and in open position.
Figure 7:
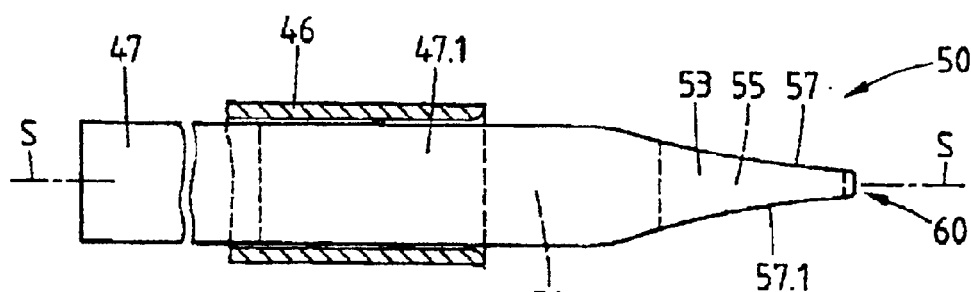
FIG. 7 is a side view of the probe shown in FIG. 6 with the rod and the grasping element.
Figure 8:
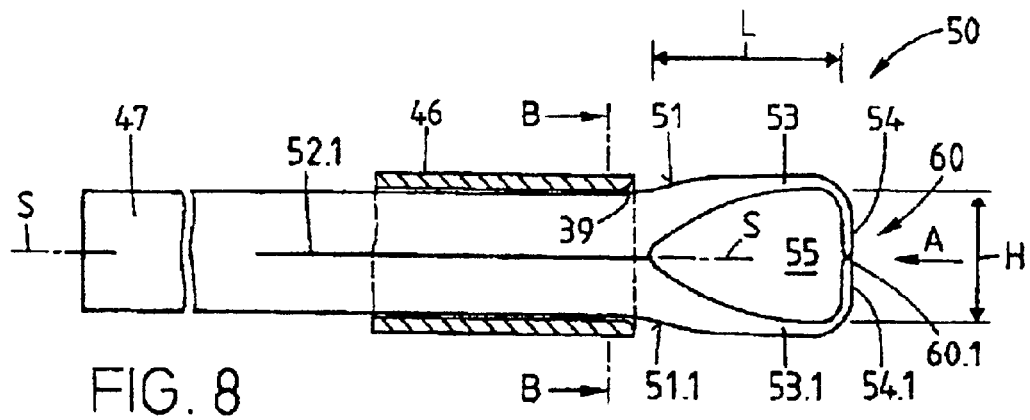
FIG. 8 is a section of the probe according to FIG. 6 with the rod and the grasping element.

FIG. 6 to FIG. 8 each shows on an enlarged scale, a section of the tube shaped probe 46 with the rod 47 co-axially disposed therein. In this embodiment, the rod 47 is configured as an elongated, unitary cylindrical body which, at the portion that projects from the probe 46, is provided with the first variation of a head piece 50 in open position. The inside of the front end of probe 46 is provided with a chamfer 39.

The head piece 50 is configured in such a way that starting from its front end 60, rod 47 is axially slotted and in the area of slot 52 is divided into two axially extending portions or arms 47.1 and 47.2. To attain the spring elastic pre-tensioning, the two arms 47.1 and 47.2 are spread or bent open relative to each other or respectively relative to the symmetrical axis S—S, thereby forming slot 52 between the two arms 47.1 and 47.2 in longitudinal direction. In this position, the two arms 47.1 and 47.2 at each of their opposing sides in the direction of the head piece 50 are configured as inclined sliding surfaces 51 and 51.1 (FIG. 6). The sliding planes 51 and 51.1 each are configured either as continually straight or as arcuate and inclining.

In the front area, the one arm 47.1 is provided with a first recess 55.1, which on its inner side is bounded at the front by a first arcuate shaped wall 53 with a leg 54 integrally formed thereon. The other arm 47.2 is provided with a second recess 55.2 which on its inner side is bounded by an arcuate shaped second wall 53.1 with a leg 54.1 integrally formed thereon. At the ends facing each other, the two legs 54 and 54.1 are each provided with an edge 56 and 56.1. In closed position, the two edges 56 and 56.1 are pressed flush against each other perpendicular to the symmetrical axis S—S (FIG. 8) forming a commissure 60.1.

FIG. 7 shows a portion of the tube shaped probe 46 and supported therein. the rod 47 with the integrally formed head piece 50 shown in side view. The head piece with recess 55 oriented perpendicular to the symmetrical axis S—S is configured starting from the front side 60 in direction of the cylindrical portion of rod 47 extending in a flaring shape, wherein the two opposite side walls 57 and 57.1 of the two walls 53 and 53.1 are configured either straight or in arcuate form.

FIG. 8 shows the probe 46 with rod 47 with the integrally formed headpiece 50 in closed position and the recess 55. The axial interior measured length L relative to the symmetrical axis S—S of the recess 55 formed by the two arcuate recesses 55.1 and 55.2 is larger than its interior measured width H. When the head piece 50 is in closed position, the opposing inner edges (not designated by a numeral) of the two arms 47.1 and 47.2 are flush pressed together and slot 52 (FIG. 6) appears as a commissure 52.1. The two legs 54 and 54.1 form at the front end 60 the commissure 60.1.

Figure 9:
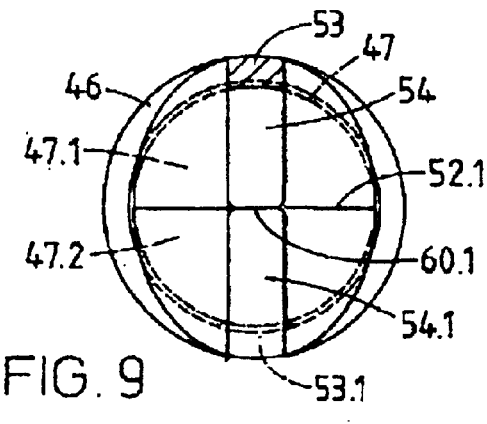
FIG. 9 is a front view of the grasping element along the arrow A in FIG. 8 disposed in the probe with the rod.

FIG. 9 shows a front view of the head piece 50 on an enlarged scale along arrow A of FIG. 8 with the first leg 54 shown in a cross sectional and partially cutaway view and the second leg 54.1 opposite thereto, both integrally formed with the two arms 47.1 and 47.2 of rod 47 (FIG. 6). In the closed position the correspondingly opposing edges 56 and 56.1 of the two legs 54 and 54.1 are pressed together flush along the commissure 60.1. Further shown in FIG. 9 is the cylindrical rod 47 which is disposed within the tube shaped probe 46 and the commissure 52.1 formed by the slot 52.

Figure 10:
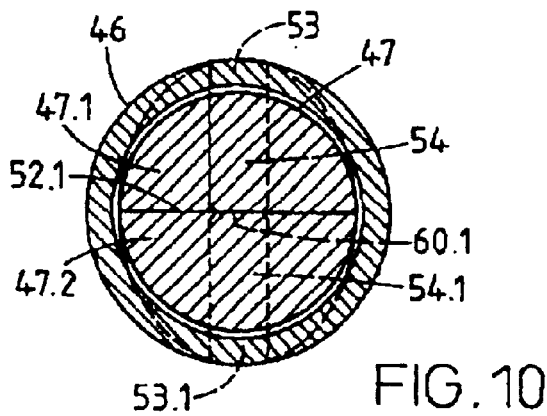
FIG. 10 is a section view of the probe with the rod and the grasping element along line B—B in FIG. 8.

FIG. 10 shows a section along line B—B of FIG. 8 with the tube shaped probe 46, and co-axially disposed therein the rod 47 with the two arms 47.1 and 47.2 separated by the slot 52 and the two legs 54 and 54.1 which are pressed together flush in the area of commissure 60.1

In another embodiment shown in FIG. 11, the rod 47 has a head piece 50 shown in a front view, and in FIG. 12 the rod 47 is shown as a profile cross section along line C—C in FIG. 11. The head piece 50 integrally formed at the front end of rod 47 with parts 53 and 53.1 and 54 and 54.1 is configured according to the head piece 50 as described in connection with FIG. 6 and FIG. 8. In a variation of the embodiment (FIG. 6 to FIG. 8) the rod 47, in accordance with FIG. 11 and FIG. 12, comprises two parts 48 and 48.1 configured each with a semicircular profiled cross section. At their distal ends, the two parts 48 and 48.1 are connected to each other by means of a laser weld. At their proximate end, the two semicircular profiled parts are separated as arms 48 and 48.1 by axial slot 52 and spread apart relative to each other for spring elastic pretensioning.

FIG. 13 shows a section of the tube shaped probe 46 and the rod 47 co-axially disposed therein on an enlarged scale. The head piece 50 configured as a second variation in an open position is seen at the front end of rod 47. The rod 47 is divided into two arms 47.1 and 47.2 by means of the slot 52 and at their opposing corresponding sides each is provided with gliding planes 51 and 51.1. that are inclining in the direction of the head piece 50. The two arms 47.1 and 47.2 are spread apart or bent open relative to each other respectively relative to the symmetrical axis S—S. At the front area, arm 47.1 is provided with a recess 55.1 which is frontally bounded by an interiorly circular arc profiled first wall and a leg 54 integrally formed thereon. The other arm 47.2 is provided with a second recess 55.2, which is frontally bounded by an interiorly circular arc profiled wall 53.1 and a leg 54.1 integrally formed thereon. In the closed position of the headpiece 50, the two recesses 55.1 and 55.2 form recess 55.

FIG. 14 shows the probe 46 with the rod 47 co-axially disposed therein and the headpiece 50 with the recess 55. In closed position (FIG. 14) the opposing ends (not designated) of the two frontal legs 54 and 54.1 are pressed flush against each other. In this variation the inside measured axial length L of recess 55 of headpiece 50 is smaller than the inside measured width H of the recess 55.

Figure 15:
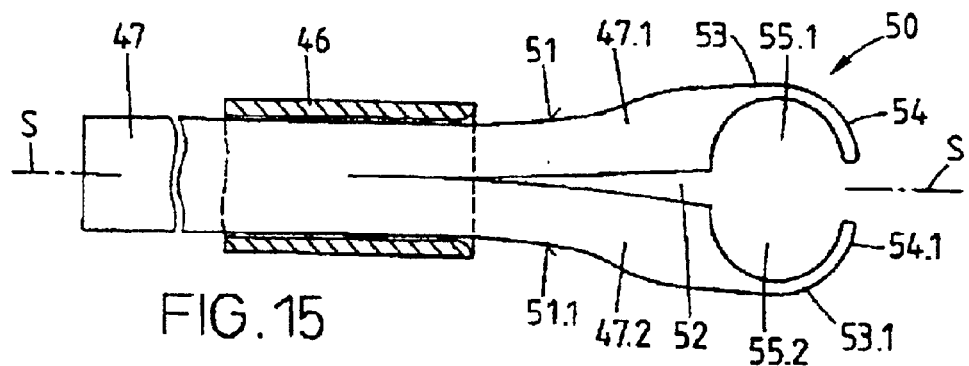
FIG. 15 is a section view of the probe according to FIG. 6 with a further variation of the grasping element disposed at the rod in an open position.
Figure 16:
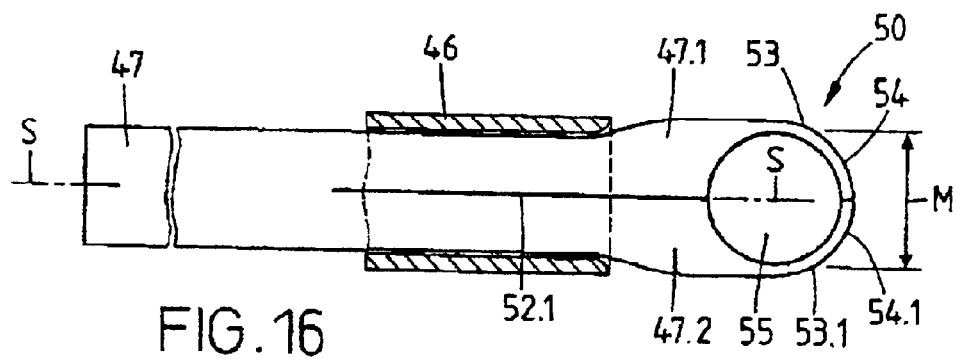
FIG. 16 is a view of the probe of FIG. 15 with the grasping element in a closed position.

Shown in FIG. 15 and FIG. 16 is a third variation of the rod 47 axially disposed in the tube shaped probe 46, wherein the rod with the integrally formed head piece 50 is divided by a slot 52 in axial direction into two arms 47.1 and 47.2. Each of the elements of rod 47 and the headpiece 50 are substantially similar to the embodiment described in connection with FIG. 13 and FIG. 14. In a variation of that embodiment, the recesses 55.1 and 55.2 of arms 47.1 and 47.2 and the two walls 53 and 53.1 with legs 54 and 54.1 are configured in a semicircular shape. In the closed position (FIG. 16) the two frontal legs 54 and 54.1 are pressed together flush at their frontal ends (not designated), In this variation the inside diameter M of recess 55 is approximately equal to the outer diameter of about 1.0 mm of the tube shaped probe 46.

Figure 17:
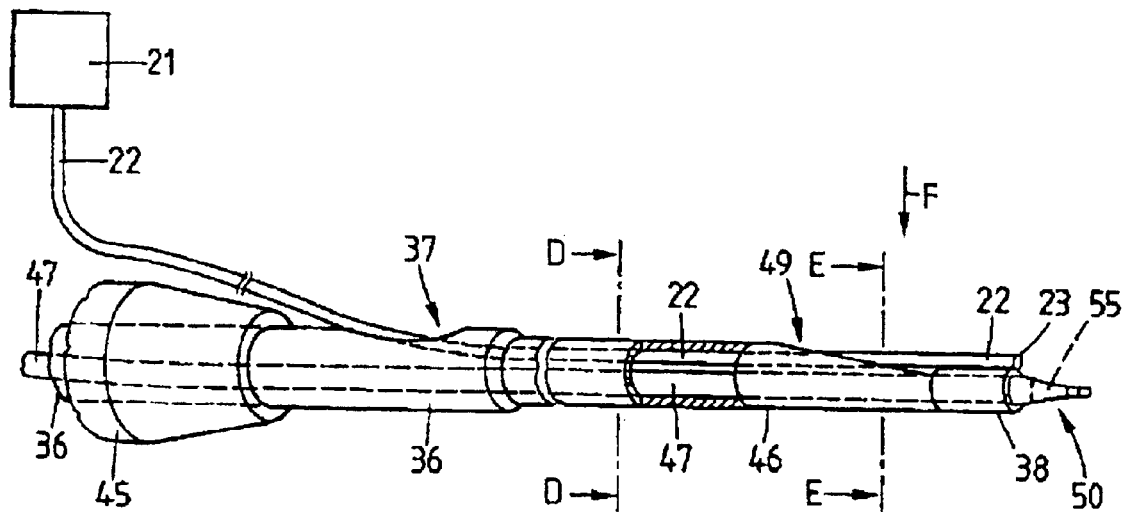
FIG. 17 is a partial 3-dimensional view with a partial sectional view of a further variation of the functional unit of the ophthalmologic instrument of FIG. 3.

In FIG. 17, a further variation is shown in a 3-dimensional view of the ophthalmologic instrument 25 (FIG. 3) with functional unit 35 in threaded engagement with the guide sleeve 45. This variation differs from the embodiment as depicted in FIG. 4 and FIG. 5 in that a first tube piece 36 is supported at one end of the probe 46 and at the other end a second tube piece 38 is attached to probe 46. The front end of rod 47 with the head piece 50 is configured as a catching element which is co-axially supported in the second tube piece 38 and projects eccentrically through the probe 46 which is configured as a hollow needle and the first tube piece 36. The first tube piece 36 with probe 46 and the second tube piece 38 together with the actuator 40 as depicted in FIG. 4 and FIG. 5, form a unit which is slidable in axial direction.

In the area of the guide sleeve 45 an inlet opening 37 is provided which corresponds to the dimension of a light guide 22 in the first tube piece 36 through which the light guide 22 is inserted into the interior space 46.1 (FIG. 18) of probe 46. As depicted schematically in FIG. 17, the light guide 22 which is projecting from the exit opening 49 is exteriorly disposed at second tube piece 38 in such a manner that the light emitted at the front side 23 is illuminating the recess 55 of head piece 50.

The light guide 22 is connected to a light source 21 schematically depicted in FIG. 17. The light source 21 is for example a battery disposed in the housing 24 of instrument 25 (FIG. 3). In a further variation, the light guide 21 may be directly connected to an ophthalmologist unit, which is not shown here in detail.

Figure 18:
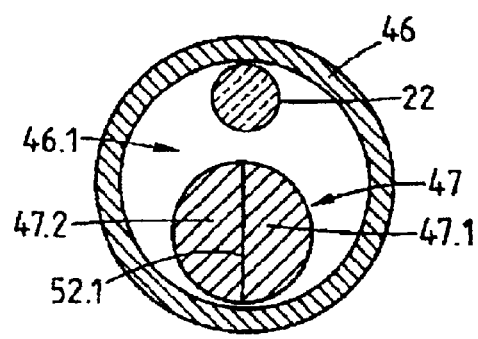
FIG. 18 is a section of a partial view along line D—D in FIG. 17 of the probe with the rod disposed therein and a light guide.

FIG. 18 shows a section along line D—D of the probe 46 on an enlarged scale with the eccentrically disposed rod 47 and the two arms 47.1 and 47.2 both shown in a profiled cross section and a light guide 22 which is likewise eccentrically disposed in the interior space 46.1

Figure 19:
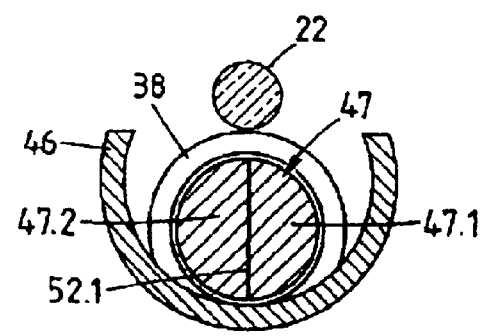
FIG. 19 is a section of a partial view along line E—E of FIG. 17 with the rod and the respective light guide.

FIG. 19 shows a section on an enlarged scale along the line E—E of the second tube piece of FIG. 17 and the rod 47 co-axially disposed therein and a light guide 22 which is disposed at the exterior of the tube piece 38.

Figure 20:
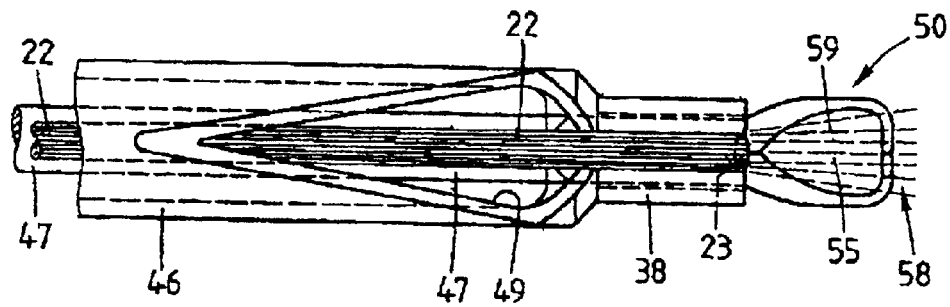
FIG. 20 is a top view along arrow F in FIG. 17 of the partial front piece of the probe with the light guide and the head piece configured as a grasping element.

In FIG. 20, the frontal part is shown in a top view on an enlarged scale along arrow F in FIG. 17 and the tube shaped probe 46 with an exit opening 49 and the second tube piece 38 disposed thereon with the head piece 50 in closed position. Further shown in FIG. 20 is the light guide 22 disposed at the frontal tube piece and projecting through the outlet opening 49. The light guide 22 can be attached to the second tube piece 38 by means not shown here in detail. The light guide 22 is preferably provided with a frontal side 23 that is sloped relative to a longitudinal axis, by means of which the light rays 59 of the light bundle 58 at a restricted spatial angle can be directed to the recess 55 of the head piece 50. In another embodiment, a lens is disposed at the frontal side 23 of light guide 22 or the light guide itself is configured as a lens.

As shown in FIG. 20, the frontal side 23 of the light guide which is disposed at the exterior of the second tube piece 38 is flush relative to the frontal side (not designated) of the second tube piece 38.

It should be understood that each of the described variations relating to the FIGS. 6–16 of the rods generally referenced as 47 and the head pieces generally referenced as 50 are likewise applicable with the embodiments of FIG. 17 to FIG. 20.

The rod 47 which is supported in probe 46 which is configured as a hollow needle is preferably fixed at the actuator 40 by means of a set screw 43 (FIGS. 4, 5) such that the head piece 50 configured with recess 55 for grasping, retaining and holding of blood vessel 12 as schematically depicted in FIG. 2 is well visible to the ophthalmologist.

Other variations, modification and structural changes of the device as set forth above are within the realm of persons skilled in the art.

While the invention has been illustrated and described as embodied in an ophthalmologic device for microsurgery, it is not intended to be limited to the details shown since various modifications and structural changes may be made without departing in any way from the spirit of the present invention.

What is claimed is:

1. An ophthalmologic instrument for microsurgery in an eye comprising:
    a housing configured as a handle and a functional unit disposed thereon and an actuator supported within the housing in operative engagement with a sliding pin and connected with the functional unit; and
    a tube shaped probe which extends into a head piece and is movable in axial direction relative thereto for operative engagement with the functional unit; and
    a rod which is axially supported within the probe which extends into a head piece configured as a holding element and having two arms separated by a slot, the two arms are configured with distal end portions which are oriented substantially at a transverse axis relative to a longitudinal axis and delimiting a recess opposing one another and are movable relative to one another into an elastic pre-tensioning first position wherein both arms are spread apart and a second position wherein the end portions terminate into opposing end faces, which when both arms are pressed together form a flush closure such that the two opposing recesses are formed together into a common recess for freely retaining and holding micro structures without squeezing or pinching the microstructures, and wherein the two arms, starting from the cylindrical rod in direction of the frontal face of the head piece viewed from the transverse axis, are tapered off with opposing outside walls of the taper configured in one of a straight or an arcuate shape.

2. The microsurgical instrument of claim 1, further comprising a light guide connected to a light source and coordinated with the headpiece which projects from the probe in the direction of the common recess formed by the two arms.

3. The microsurgical instrument of claim 2, wherein the light guide has a front face from which light rays can emanate and be directed to the recess.

4. The microsurgical instrument of claim 2, wherein the front face of the light guide is configured as a convex optical lens.

5. The microsurgical instrument of claim 4, wherein the front face of the light guide is provided with an optical lens.

6. The microsurgical instrument of claim 2, wherein the front face of the light guide is configured in slanted relationship to the longitudinal axis of the light guide, which is directed toward the recess.

7. The microsurgical instrument of claim 2, wherein the tube shaped probe is configured for receiving the rod and the light guide and provided at one end with a first tube shaped piece supported in a guide sleeve and at the other end provided with a second tube shaped piece for co-axially supporting the rod.

8. The microsurgical instrument of claim 7, wherein the probe with the first tube piece and the second tube piece are formed as a unit which is axially movable relative to the head piece provided with the stationary rod.

9. The microsurgical instrument of claim 7, wherein the first tube piece is provided with an inlet opening for insertion of the light guide is formed at the upper portion of the probe and axially at a distance an exit opening for exiting of the light guide.

10. The microsurgical instrument of claim 9, wherein the end of light guide exiting from the opening is disposed at the outer wall of the second tube piece.

11. The microsurgical instrument of claim 1, wherein each of the recesses are bounded frontally by claw-like shaped legs integrally formed at the two arms and configured in such a way that when the arms are brought into a closed position, opposing edges of the legs can be pressed together for a flush closure.

12. The microsurgical instrument of claim 11, wherein each of the legs are provided with an edge which oppose one another and which are of a size smaller than one half the diameter of the rod having a cylindrical shape.

13. The microsurgical instrument of claim 1, wherein the recess of each of the arms starting from a frontal leg thereof in direction of the slot is arcuately shaped such that in a closed position the common recess has the shape of a tear drop.

14. The microsurgical instrument of claim 13, wherein an inside length of the tear drop shaped recess is greater than the inside width of the tear drop shape.

15. The microsurgical instrument of claim 1, wherein the recess of each of the arms each starting from a frontal leg thereof in axial direction of the slot is arcuately shaped such that in a closed position the common recess has an elongated shape.

16. The microsurgical instrument of claim 15, wherein the inside length of the elongated common recess oriented in axial direction of the headpiece is smaller than then the inside width, which is oriented perpendicularly thereto.

17. The microsurgical instrument of claim 1, wherein the recess of each arm each starting from a frontal leg thereof in axial direction of the slot is arcuately shaped such that in a closed position the common recess has a circular shape.

18. The microsurgical instrument of claim 17, wherein the inside diameter of the circular shaped common recess is substantially the same as the outer diameter of the tube shaped probe.

19. The microsurgical instrument of claim 1, wherein the cylindrical rod comprises two portions connected to each other, each of the portions having a profile cross section configured in semicircular shape which extend at one end into a head piece of claw-like configuration and a recess.

* * * * *